United States Patent [19]

Konai et al.

[11] Patent Number: 4,825,007
[45] Date of Patent: Apr. 25, 1989

[54] OXIDATION PROCESS OF AROMATIC COMPOUNDS

[75] Inventors: Yutaka Konai; Kazuo Yoshida; Masatoshi Hino, all of Iwaki, Japan

[73] Assignee: Kureha Kagaku Kogyo K.K., Japan

[21] Appl. No.: 116,734

[22] Filed: Nov. 4, 1987

[30] Foreign Application Priority Data

Nov. 7, 1986 [JP] Japan .................................. 61-263840

[51] Int. Cl.$^4$ ............................................. C07C 27/16
[52] U.S. Cl. .................................................. 568/815
[58] Field of Search ................................. 568/803, 815

[56] References Cited

U.S. PATENT DOCUMENTS 4,746,757  5/1988  Terauchi et al. .................... 568/815

FOREIGN PATENT DOCUMENTS 218866  7/1969  U.S.S.R. ............................... 568/910

Primary Examiner—Werren B. Lone
Attorney, Agent, or Firm—Lowe, Price, LeBlanc, Becker & Shur

[57] ABSTRACT

An aromatic compound selected from benzene and biphenyl compounds containing at least one isopropyl group is oxidized to convert at least one of the at least one isopropyl group into a 2-hydroxy-2-propyl group. The oxidation of the aromatic compound is effected with molecular oxygen in the presence of an aqueous alkali solution in an oxidative reaction vessel made of nickel at parts thereof where the vessel comes into contact with a reaction mixture. In particular, the above process suppresses the formation of by-products and permits long-term oxidation on an industrial scale.

13 Claims, No Drawings

OXIDATION PROCESS OF AROMATIC COMPOUNDS

BACKGROUND OF THE INVENTION

1. Field of the Invention

This invention relates to a process for the oxidation of an aromatic compound selected from benzene and biphenyl compounds containing at least one isopropyl group, in which the aromatic compound is oxidized with molecular oxygen to convert at least one of said at least one isopropyl group into a 2-hydroxy-2-propyl group.

The benzene or biphenyl compound, which is prepared in accordance with the process of this invention and contains at least one 2-hydroxy-2-propyl group, can be converted into a benzene or biphenyl compound containing at least one hydroxyl group bonded directly to the aromatic ring by a process similar to that disclosed in the specification of Japanese Patent Application No. 123819/1985 on naphthalene derivatives. It is therefore possible to prepare, for example, hydroquinone from p-diisopropylbenzene or resorcine from m-diisopropylbenzene by practising successively the process of this invention and a process similar to that disclosed in the specification of Japanese Patent Application No. 123819/1985 on naphthalene derivatives.

2. Related Art

A variety of processes, including those to be described below by way of example, has heretofore been known to oxidize one or more side-chain isopropyl groups of a benzene ring with molecular oxygen in the presence of an aqueous alkali solution so as to convert said one or more side-chain isopropyl groups into the corresponding number of 2-hydroxy-2-propyl groups.

(1) Cumene or diisopropylbenzene is oxidized in the presence of an aqueous sodium carbonate solution and cobalt naphthenate to obtain a 2-hydroxy-2-propyl derivative [JOURNAL OF THE FUEL SOCIETY OF JAPAN, 35, 518–525 (1956)].

(2) An aryldialkylmethane is oxidized in the presence of an aqueous caustic alkali solution and a manganese salt to obtain an α-aryl tertiary alcohol (Japanese Patent Publication No. 19355/1964).

(3) A tertiary hydrogen is oxidized in the presence of an aqueous caustic alkali solution to obtain an aralkyl carbinol (Japanese Patent Publication No. 21242/1964).

(4) Diisopropylbenzene is oxidized in the presence of an aqueous caustic alkali solution to obtain a 2-hydroxy-2-propyl derivative (Japanese Patent Laid-Open No. 59827/1976).

(5) An aryldialkylmethane is oxidized in the presence of an aqueous alkali solution, and the feeding of oxygen is stopped and the reaction mixture is heated, thereby decomposing a hydroperoxide byproduct and obtaining an α,α-dialkylbenzylalcohol (Japanese Patent Laid-Open No. 162539/1983).

(6) An aryldialkylmethane is oxidized in the presence of an aqueous alkali solution and a transition metal compound to obtain an α-aryl tertiary alcohol (Japanese Patent Laid-Open No. 162540/1983).

(7) Diisopropylbenzene is oxidized in the presence of an aqueous alkali solution to obtain a mixture composed principally of a dihydroperoxide, followed by reduction of the mixture to obtain di(2-hydroxy-2-propyl)benzene (Japanese Patent Laid-Open Nos. 149538/1985, 152431/1985 and 85340/1986). By these processes, the conversion of one or more side-chain isopropyl groups of a benzene ring into the corresponding number of 2-hydroxy-2-propyl groups has been effected.

However, each of the above processes (1), (2) and (6) results in considerable coloration of its reaction product due to the use of the transition metal compound, thereby making it difficult to purify the intended compound. The above process (3) uses the aqueous caustic alkali solution of a high concentration in order to suppress the byproduction of hydroperoxides. The process (3) is however not considered to be able to inhibit the byproduction of such hydroperoxides completely. The above process (4) is not considered to be an effective process for general purposes, because the composition of its raw materials is limited. The above process (5) is disadvantageous from the viewpoint of production cost, since heating is effected after completion of the oxidative reaction in order to suppress the byproduction of hydroperoxides like the process (3). The above process (7) is disadvantageous economically, because it requires accumulation of the instable hydroperoxide at a high concentration, the byproduction of ketone compounds due through decomposition of the hydroperoxide is not ignorable, and the two-step reaction is carried out.

SUMMARY OF THE INVENTION

An object of this invention is to develop a process for the oxidation of an aromatic compound selected from benzene and biphenyl compounds containing at least one isopropyl group, said process including oxidizing the aromatic compound to convert at least one of said at least one isopropyl group into a 2-hydroxy-2-propyl group, which is free of the above-described drawbacks of the prior art processes and can suppress the formation of hydroperoxide as byproducts to prepare a high-purity benzene or biphenyl compound containing at least one 2-hydroxy-2-propyl group.

The above object of this invention can be achieved by a process for the oxidation of an aromatic compound selected from benzene and biphenyl compounds containing at least one isopropyl group, said process including oxidizing the aromatic compound to convert at least one of said at least one isopropyl group into a 2-hydroxy-2-propyl group, which comprises oxidizing the aromatic compound with molecular oxygen in the presence of an aqueous alkali solution in an oxidative reaction vessel made of nickel at parts thereof where the vessel comes into contact with a reaction mixture.

When the oxidation is carried out in accordance with the process of this invention, namely, with molecular oxygen in the presence of an aqueous alkali solution in an oxidative reaction vessel made of nickel at parts thereof where the vessel comes into contact with a reaction mixture, the formation of byproducts can be minimized and especially, the formation of hydroperoxides can be avoided practically.

DETAILED DESCRIPTION OF THE INVENTION

More specifically describing, the oxidation process of this invention comprises the following consecutive steps:

(a) oxidizing the aromatic compound with molecular oxygen in the presence of an aqueous alkali solution in an oxidative reaction vessel made of nickel at parts thereof where the vessel comes into contact with a reaction mixture;

(b) separating and recovering the aqueous alkali solution from the reaction mixture after the oxidative reaction (a), thereby collecting a solid matter;
(c) washing the solid matter with water so as to leach and eliminate carboxylic acids byproduced in the oxidative reaction (a);
(d) extracting the remaining solid matter with benzene or an alkyl benzene having at least one $C_{1-3}$ side chain; and
(e) cooling the resulting extract to isolate an aromatic compound selected from benzene and biphenyl compounds containing at least one 2-hydroxy-2-propyl group.

Certain features of the process of this invention will hereinafter be described in detail.

(Oxidation reactor made of nickel)

It is a fundamental feature of the process of the present invention that one or more side-chain isopropyl groups of a benzene or biphenyl ring are oxidized with molecular oxygen in the presence of an aqueous alkali solution by using an oxidation reactor made of nickel at parts thereof where the oxidation reactor comes into contact with a reaction mixture. Incidentally, the material of an oxidation reactor is not referred to at all in any of JOURNAL OF THE FUEL SOCIETY OF JAPAN, 35, 518–525 (1956) (1), Japanese Patent Publication No. 19355/1964 (2), Japanese Patent Laid-Open No. 59827/1976 (3), Japanese Patent Laid-Open No. 162539/1983 (5), and Japanese Patent Laid-Open Nos. 149538/1985, 152431/1985 and 85340/1986 (7), among the conventional processes described above. A resin-made oxidation reactor is used in the Examples of Japanese Patent Publication No. 21242/1964 (3). In the Examples of Japanese Patent Laid-Open No. 162540/1983 (6), it is described to the effect that a glass-made flask was used as an oxidation reactor. A conclusion can hence be derived that it was not known at all in the prior art to use nickel as a material for an oxidation reaction for practising industrially a reaction in which one or more side-chain isopropyl groups of a benzene or biphenyl ring are oxidized with molecular oxygen in the presence of an aqueous alkali solution to convert same into the corresponding number of 2-hydroxy-2-propyl groups. By the way, the term "nickel" as used herein means nickel or nickel steel having a pure nickel content of 75 wt. % or higher.

Upon oxidation of one or more side-chain isopropyl groups of a benzene or biphenyl ring with molecular oxygen in the presence of an aqueous alkali solution so as to convert the isopropyl groups into the corresponding number of 2-hydroxy-2-propyl groups, the reaction is carried out under severe conditions that the aqueous alkali solution of a high concentration and oxygen exist concurrently. Selection of a material for the oxidation reactor is hence most critical. Materials such as SUS, titanium and glass lining cannot withstand the oxidative conditions of the process of this invention. If a SUS-made reactor should be used, the inner wall of the reactor is attacked, namely, corroded to such an extent that the resulting corrosion is visible to the naked eyes, the reaction product is stained by heavy metals leached out so that the reaction product is tinged in a reddish brown color, and the yield of the intended 2-hydroxy-2-propyl derivative is lowered. Use of a titanium-made reactor can provide a satisfactory yield but powder of titanium oxide is inevitably admixed in the reaction mixture. A glass-lined reactor cannot withstand long-term use against any high-concentration alkali. As a result of an investigation conducted by the present inventors, a fact totally unknown in the past has been revealed that a nickel-made oxidation reactor can withstand over a long period of time even in a heating and stirring operation in the presence of both high-concentration aqueous alkali solution and oxygen and can hence be used as an industrial oxidation reactor.

For the practice of the process of this invention, nickel is used as a material for parts of an oxidation reactor where the oxidation reactor comes into contact with a reaction mixture. The term "parts where the oxidation reactor or vessel comes into contact with a reaction mixture" as used herein embraces the inner wall of the reactor, an oxygen or oxygen-containing gas inlet tube, an upper reflux condenser, a gas outlet, stirring blades and shaft, baffles, thermometer sheath or well, valves, and the like. These parts may be made of nickel or alternatively, may be fabricated by relying upon a suitable processing method chosen from nickel lining, nickel spray coating and nickel plating. Since SUS can successfully withstand an aqueous alkali solution of a high concentration provided that oxygen does not exist at the same time, SUS-made pipes and valves may be used for transferring the reaction mixture before and after the reaction.

(Aromatic compound)

For the practice of the process of this invention, is employed as a starting material an aromatic compound selected from benzene and biphenyl compounds having at least one side-chain isopropyl group. As exemplary benzene-ring containing compounds, may be mentioned cumene, p-diisopropylbenzene and m-diisopropylbenzene. Illustrative examples of the biphenyl-ring containing compound may include 3-isopropylbiphenyl, 4-isopropylbiphenyl and 4,4'-diisopropylbiphenyl.

(Aqueous alkali solution)

In order to practise the process of this invention, sodium hydroxide or potassium hydroxide may preferably be used as an alkali. Although the velocity of the oxidation is somewhat faster when potassium hydroxide is used, a satisfactory yield is still available from the use of sodium hydroxide. The aqueous alkali solution can be used repeatedly. It is only necessary to replenish an alkali hydroxide in such an amount that is approximately equal to that consumed by a small amount of carboxylic acids byproduced in the reaction. It is hence extremely economical. Since the alkali salts of the byproduced carboxylic acids are substantially insoluble in the aqueous alkali solution of the high concentration and thus precipitate as crystals, they can be eliminated easily from the reaction system. This tendency is particularly remarkable when sodium hydroxide is used.

For the practice of the process of this invention, an aqueous alkali solution in a concentration range of 20–70 wt. %, preferably, 30–50 wt. % is used. Any alkali concentrations lower than the lower limit will result in byproduction of ketones in unignorably high yields. If the alkali concentration should exceed the upper limit, the viscosity of the reaction mixture will become so high that difficulties will be encountered in stirring the reaction mixture.

Upon practice of the process of this invention, the oxidation is carried out by mixing the aromatic compound and aqueous alkali solution to give a weight ratio of 1:100–10:1, preferably, 1:10–5:1. It is to ensure smooth stirring during the oxidation that must be taken into due consideration upon determination of the amount of the aqueous alkali solution to be used. Where the reaction product is solid at the reaction temperature, the stirring becomes more difficult as the reaction proceeds. It is therefore necessary to determine the amount of the aqueous alkali solution to be used, while taking into consideration the degree of oxygen to be supplied and difficulties to be encountered in transferring the reaction product after the reaction.

(Reaction temperature)

In order to practise the process of this invention, the oxidation is carried out at a temperature in a range of 90°–150° C., preferably, 110°–130° C. If the reaction temperature should be lower than the lower limit, more hydroperoxides will be byproduced. On the other hand, any reaction temperatures higher than the upper limit will result in more byproduction of carboxylic acids.

(Oxygen partial pressure, and total pressure in the reactor)

In order to practise the process of this invention, the oxidation is carried out at an oxygen partial pressure of 0.2–30 kg/cm$^2$. Although the velocity of the oxidation becomes higher as the oxygen partial pressure increases, the rate of the velocity increase is small. It is hence practical to conduct the oxidation at the highest oxygen partial pressure within a pressure range feasible in view of economy, safety and operability. As the molecular oxygen in this invention, it is possible to use not only oxygen gas but also a mixed gas of oxygen gas and an inert gas or air without any problems. The total pressure in the reactor may preferably be set at normal pressure - 30 kg/cm$^2$. This total pressure is determined in accordance with the same standard as that relied upon for the determination of the oxygen partial pressure. It is thus practical to conduct the oxidation at the highest total pressure within a total pressure range feasible in view of economy, safety and operability.

(Reaction method)

For the practice of the process of this invention, the oxidation is carried out at the above temperature and pressure for 2–40 hours, preferably, 5–30 hours. The object can be achieved within the above time range so long as the stirring and the supply of oxygen are effected without problems, although the velocity of the oxidation varies depending on the starting compound.

The batch process, semi-batch process and continuous process may all be used to practise the process of the present invention. Since the batch process results in the generation of significant heat immediately after the initiation of the reaction and more carboxylic acids are formed due to localized temperature increases caused accordingly, the semi-batch or continuous process is more preferable. When the feeding rate of the starting material is controlled suitably in the semi-batch or continuous process, the byproduction of carboxylic acids is lowered and in contrast, the yield of the intended compound is conveniently increased.

Particularly good results can be obtained from a practice of the process of this invention, provided that an oxidation reactor made of nickel at parts where the reactor comes into contact with a reaction mixture is used and as reaction conditions, an aqueous alkali solution having a concentration in the range of 20–70 wt. %, a reaction temperature in the range of 90°–150° C. and an oxygen partial pressure in the range of 0.2–30 kg/cm$^2$ are chosen as described above.

When an aromatic compound selected from benzene and biphenyl compounds containing two or more isopropyl groups is used as a starting material upon practice of the present invention, the reaction product is a mixture of two or more compounds having different numbers of 2-hydroxy-2-propyl groups respectively since the velocity of oxidation of the first isopropyl group is different from the velocity of oxidation of the second or any further isopropyl group. In such a case, the compounds can be separated by making use of the fact that their solubility levels in an organic solvent differ in accordance with the numbers of their 2-hydroxy-2-propyl groups. When p-diisopropylbenzene is oxidized by way of example in accordance with the process of this invention, the reaction mixture obtained after removal of byproduced carboxylic acids is composed of p-diisopropylbenzene, p-(2-hydroxy-2-propyl)-cumene and p-di(2-hydroxy-2-propyl)benzene. When this mixture is dissolved under heat in benzene or an alkylbenzene having a $C_{1-3}$ side chain and then cooled, p-di(2-hydroxy-2-propyl)benzene is solely allowed to crystallize out at a high recovery rate and in a high purity. Since a mixture, which is obtained by eliminating the alkylbenzene from the liquid phase resulting subsequent to the removal of p-di(2-hydroxy-2-propyl)benzene, can be used as a starting material for the oxidative reaction by adding p-diisopropylbenzene, the starting material is lost only as byproduced carboxylic acids throughout the process of this invention.

ADVANTAGES OF THE INVENTION

As a first advantage brought about by the process of this invention in which one or more side-chain isopropyl groups of a benzene or biphenyl ring are oxidized with molecular oxygen in the presence of an aqueous alkali solution into the corresponding number of 2-hydroxy-2-propyl groups by using an oxidation reactor made of nickel at parts where the reactor comes into contact with a reaction mixture, may be mentioned that a long-term oxidation can be carried out on an industrial scale. As a second advantage which is more important, may be mentioned that the proportions of hydroperoxides formed in a reaction mixture can be lowered to practically-ignorable levels. This advantage has not been known to date.

It has been proposed to use a great deal of a transition metal such as cobalt or manganese as a catalyst upon oxidation of one or more side-chain isopropyl groups of a benzene ring [for example, JOURNAL OF THE FUEL SOCIETY OF JAPAN, 35, 518–525 (1956), Japanese Patent Publication No. 19355/1964, and Japanese Patent Laid-Open No. 162540/1983). Use of a transition metal such as cobalt or manganese in a large amount can cause decomposition of hydroperoxides and can hence reduce the amounts of the hydroperoxides contained in the reaction mixture. The reaction product is however stained by such a transition metal as already mentioned above. Under the conditions chosen for the practice of the process of this invention, nickel remains extremely stable and no changes are observed on the inner wall of the reactor even after its use over a long period of time. Further, the content of nickel mixed in the reaction product is as little as 1 ppm or less and the stain of the reaction product by the transition metal can hence be ignored. It is practically possible to consider that no chemical corrosion has taken place.

Although the possibility of accelerated decomposition of hydroperoxides by a trace amount of nickel cannot be negated completely, it is more likely that nickel has taken no part in the decomposition and formation of hydroperoxides, in view of the fact that a trace amount of a transition metal rather accelerates the formation of hydroperoxides, the velocity of formation of hydroperoxides is far slower in the case of nickel compared with cobalt or manganese, and almost no hydroperoxides are contained in the reaction product. As will be demonstrated in Comparative Example 3, use of a low reaction temperature leads to the formation of hydroperoxides in unignorable amounts even when a reactor made of nickel is employed. On the other hand, there is a fact that hydroperoxides are not detected when the reaction temperature is sufficiently high. In the reaction in which one or more side-chain isopropyl groups of a benzene or biphenyl ring are oxidized with molecular oxygen in the presence of an aqueous alkali solution, hydroperoxides are not formed by nature so long as suitable reaction conditions are selected. As possible reasons for the failure in inhibiting the formation of hydroperoxides completely in the prior art, it may be mentioned that a reactor made of a material inert under the reaction conditions was not used as a reactor and the selection of reaction conditions was inappropriate. Since highly-inert nickel is used as a material for a reactor and suitable reaction conditions have been chosen in the process of this invention, the reaction in which one or more side-chain isopropyl groups of a benzene or biphenyl ring are oxidized with molecular oxygen in the presence of an aqueous alkali solution is allowed to proceed as expected. As a result, a benzene or biphenyl compound having one or more 2-hydroxy-2-propyl groups as side chain or chains can be prepared at satisfactory levels in both yield and purity.

EMBODIMENTS OF THE INVENTION

The process of this invention will hereinafter be described in detail by the following Examples and Comparative Examples. Needless to say, the present invention is not necessarily limited to the following Examples.

EXAMPLE 1

In an autoclave made of SUS316, having an internal capacity of 1,500 ml, lined with nickel and fitted with a stirrer, a gas inlet tube, a thermometer sheath and a gas outlet tube equipped with a reflux condenser, were charged 80.0 g (0.493 mole) of p-diisopropylbenzene, 240 g of sodium hydroxide and 560 g of water. The internal temperature was raised to 120° C., at which the contents were reacted for 22 hours while agitating them vigorously and feeding oxygen at a rate of 4,000 ml per hour (STP) while maintaining the internal pressure at 3 kg/cm$^2$G. After completion of the reaction, the contents were taken out of the autoclave and filtered to separate a colorless solid matter and an aqueous alkali phase from each other. The solid matter was washed with water to remove carboxylic acids and was then dried to obtain 89.2 g of a colorless solid substance. As a result of an analysis with high-performance liquid chromatography, the solid substance was found to contain 4.2 g (0.026 mole; conversion: 94.7%) of p-diisopropylbenzene, 24.3 g (0.136 mole; yield: 27.6 mole %) of p-(2-hydroxy-2-propyl)cumene and 60.4 g (0.311 mole; yield: 63.1 mole %) of p-di(2-hydroxy-2-propyl)benzene. Formation of acetyl compounds and hydroxyperoxides was unobserved practically. The solid substance was dissolved in its entirety at 110° C. in 300 ml of toluene, hot-filtered and then allowed to cool down. Precipitated crystals were collected by filtration and then dried, thereby obtaining 58.6 g (0.302 mole; overall yield: 61.3 mole %) of colorless p-di(2-hydroxy-2-propyl)benzene in a purity of 99.8%.

COMPARATIVE EXAMPLE 1

In an autoclave made of SUS316, having an internal capacity of 200 ml, and fitted with a stirrer, a gas inlet tube, a thermometer sheath and a gas outlet tube equipped with a reflux condenser, were charged 10.0 g (0.062 mole) of p-diisopropylbenzene, 30 g of sodium hydroxide and 70 g of water. The internal temperature was raised to 120° C., at which the contents were reacted for 22 hours while agitating them vigorously and feeding oxygen at a rate of 500 ml per hour (STP) while maintaining the internal pressure at 3 kg/cm$^2$G. After completion of the reaction, the contents were taken out of the autoclave. The contents were tinged in a reddish brown color. In addition, small pits and grooves formed as a result of corrosion were observed clearly by the naked eyes in the inner wall of the autoclave. A solid matter, which had been obtained after separation of an aqueous alkali phase, was washed with water to remove carboxylic acids and was then dried to recover 8.25 g of a dry solid substance of a brown color. As a result of an analysis with high-performance liquid chromatography, the solid substance was found to contain 0.50 g (3.08 millimoles; conversion: 95.0%) of p-diisopropylbenzene, 2.25 g (0.013 mole; yield: 21.0 mole %) of p-(2-hydroxy-2-propyl)cumene and 5.31 g (0.027 mole; yield: 43.5 mole %) of p-di(2-hydroxy-2-propyl)benzene. The solid substance was subjected in its entirety to crystallization in the same manner as in Example 1 but the color was not eliminated. Pale brown p-di(2-hydroxy-2-propyl)benzene (5.05 g; 0.026 mole; overall yield: 41.9 mole %) was obtained in a purity of 97.5%.

COMPARATIVE EXAMPLE 2

In an autoclave made of titanium, having an internal capacity of 200 ml, and fitted with a stirrer, a gas inlet tube, a thermometer sheath and a gas outlet tube equipped with a reflux condenser, were charged 10.0 g (0.062 mole) of p-diisopropylbenzene, 30 g of sodium hydroxide and 70 g of water. The internal temperature was raised to 120° C., at which the contents were reacted for 22 hours while agitating them vigorously and feeding oxygen at a rate of 500 ml per hour (STP) while maintaining the internal pressure at 3 kg/cm$^2$G. After completion of the reaction, the contents were taken out of the autoclave and then filtered to separate a colorless solid matter and an aqueous alkali phase from each other. The solid matter was washed with water to eliminate carboxylic acids and was thereafter dried to recover 13.1 g of a solid colorless substance. It was attempted to dissolve the whole solid substance at 110° C. in 40 ml of toluene. Since some undissolved matter was observed, the undissolved matter was collected by hot filtration, washed with toluene and then dried to obtain 2.1 g of colorless powder. The powder did not burn and as a result of X-ray diffraction, it was found to be titanium oxide. A trace of corrosion was observed in the inner wall of the autoclave. As a result of an analysis with high-performance liquid chromatography, the reaction product obtained after the removal of the titanium oxide was found to contain 0.43 g (2.65 millimoles;

conversion: 95.7%) of p-diisopropylbenzene, 2.96 g (0.017 mole; yield: 27.4 mole %) of p-(2-hydroxy-2-propyl)cumene and 7.25 g (0.037 mole; yield mole %) of p-di(2-hydroxy-2-propyl)benzene.

COMPARATIVE EXAMPLE 3

In the same manner as in Example 1, the oxidation of 80 g (0.493 mole) of p-di-isopropylbenzene was carried out by changing the reaction temperature from 120° C. to 80° C. The reaction product obtained subsequent to its water washing and drying was a colorless solid matter whose weight was 88.1 g. Through a high-performance liquid chromatographic analysis, the solid matter was found to contain 7.7 g (0.047 mole; conversion: 90.5%) of p-diisopropylbenzene, 18.5 g (0.104 mole; yield: 21.1 mole %) of p-(2-hydroxy-2-propyl)cumene, 55.2 g (0.284 mole; yield: 57.6 mole %) of p-di(2-hydroxy-2-propyl)benzene, 1.0 g (0.006 mole; yield: 1.3 mole %) of p-acetylcumene, 1.5 g (0.008 mole; yield: 1.7 mole %) of p-(2-hydroxy-2-propyl)acetophenone, 1.3 g (0.007 mole; yield: 1.4 mole %) of p-(2-hydroperoxy-2-propyl)cumene, and 0.7 g (0.003 mole; yield: 0.6 mole%) of p-di(2-hydroperoxy-2-propyl)benzene.

EXAMPLE 2

Using 79.9 g (0.665 mole) of cumene in lieu of p-diisopropylbenzene, oxidation was carried out in the same apparatus and under the same conditions as those employed in Example 1. The reaction product obtained subsequent to its water washing and drying was an oily matter whose weight was 79.6 g. According to results of a high-performance liquid chromatographic analysis, the oily matter was found to contain 3.1 g (0.026 mole; conversion: 96.1%) of cumene and 75.3 g (0.553 mole; yield: 83.2 mole %) of dimethylphenylcarbinol. Acetophenone or cumene hydroperoxide was not formed practically.

EXAMPLE 3

Using 76.6 g (0.472 mole) of m-diisopropylbenzene in lieu of p-diisopropylbenzene, oxidation was carried out in the same apparatus and under the same conditions as those employed in Example 1. The reaction product obtained subsequent to its water washing and drying was a colorless solid matter whose weight was 80.3 g. According to results of a high-performance liquid chromatographic analysis, the solid matter was found to contain 3.5 g (0.022 mole; conversion: 95.3%) of m-diisopropylbenzene, 20.8 g (0.117 mole; yield: 24.8 mole %) of m-(2-hydroxy-2-propyl)cumene, and 54.6 g (0.281 mole; yield: 59.5 mole %) of m-di(2-hydroxy-2-propyl)benzene. The yields of acetyl derivatives and hydroperoxides were all not higher than 0.1 mole %.

EXAMPLE 4

Using 79.9 g (0.407 mole) of 4-isopropylbiphenyl in lieu of p-diisopropylbenzene, oxidation was carried out in the same apparatus and under the same conditions as those employed in Example 1. The reaction product obtained subsequent to its water washing and drying was a colorless solid matter whose weight was 80.5 g. According to results of a high-performance liquid chromatographic analysis, the solid matter was found to contain 7.7 g (0.039 mole; conversion: 90.4%) of 4-isopropylbiphenyl and 70.5 g (m.p. 93–94° C.; 0.332 mole; yield: 81.6 mole %) of 4-(2-hydroxy-2-propyl)biphenyl. The yields of acetyl derivatives and hydroperoxides were all not higher than 0.1 mole %.

EXAMPLE 5

Using 79.2 g (0.403 mole) of 3-isopropylbiphenyl in lieu of p-diisopropylbenzene, oxidation was carried out in the same apparatus and under the same conditions as those employed in Example 1. The reaction product obtained subsequent to its water washing and drying was an oily matter of a pale green color, whose weight was 79.2 g. According to results of a high-performance liquid chromatographic analysis, the oily matter was found to contain 11.7 g (0.060 mole; conversion: 85.1%) of 3-isopropylbiphenyl and 63.9 g (0.301 mole; yield: 74.7 mole %) of 3-(2-hydroxy-2-propyl)biphenyl. The yields of acetyl derivatives and hydroperoxides were all not higher than 0.1 mole %.

EXAMPLE 6

Using 79.8 g (0.335 mole) of 4,4'-diisopropylbiphenyl in lieu of p-diisopropylbenzene, oxidation was carried out in the same apparatus and under the same conditions as those employed in Example 1. The reaction product obtained subsequent to its water washing and drying was a colorless solid matter whose weight was 78.5 g. According to results of a high-performance liquid chromatographic analysis, the solid matter was found to contain 5.1 g (0.021 mole; conversion: 93.7%) of 4,4'-diisopropylbiphenyl, 28.3 g (0.111 mole; yield: 33.1 mole %) of 4-(2-hydroxy-2-propyl)-4'-isopropylbiphenyl, and 43.3 g (0. yield: 47.8 mole %) of 4,4'-di(2-hydroxy-2-propyl)biphenyl. The yields of acetyl derivatives and hydroperoxides were all not higher than 0.1 mole %. Upon recrystallization of the whole solid matter from toluene, 35.4 g of 4,4'-di(2-hydroxy-2-propyl)biphenyl was obtained (purity: 99.8%; m.p. 168°–169° C.; 0.131 mole; recovery rate of the recrystallization: 82%).

What is claimed is:

1. A process for the oxidation of an aromatic compound selected from benzene and biphenyl compounds containing at least one isopropyl group, said process including oxidizing the aromatic compound to convert at least one of said at least one isopropyl group into a 2-hydroxy-2-propyl group, which process comprises oxidizing the aromatic compound with molecular oxygen in the presence of an aqueous alkali solution in an oxidative reaction vessel, said vessel being made of nickel at parst thereof which come into contact with a reaction mixture.

2. The process as claimed in claim 1, wherein the aqueous alkali solution is a 20–70 wt. % aqueous solution of sodium hydroxide or potassium hydroxide.

3. The process as claimed in claim 1, wherein the aqueous alkali solution is a 30–50 wt. % aqueous solution of sodium hydroxide or potassium hydroxide.

4. The process as claimed in claim 1, wherein the oxidative reaction is carried out at an oxygen partial pressure of from 0.2 to 30 kg/cm$^2$.

5. The process as claimed in claim 1, wherein the oxidative reaction is carried out in a temperature range of from 90° to 150° C.

6. The process as claimed in claim 1, wherein the mixing weight ratio of the aromatic compound to the aqueous alkali solution is from 1:100 to 10:1.

7. The process as claimed in claim 1, wherein the aromatic compound is p-diisopropylbenzene.

8. The process as claimed in claim 1, wherein the aromatic compound is m-diisopropylbenzene.

9. The process as claimed in claim 1, wherein the aromatic compound is cumene.

10. The process as claimed in claim 1, wherein the aromatic compound is 4-isopropylbiphenyl.

11. The process as claimed in claim 1, wherein the aromatic compound is 3-isopropylbiphenyl.

12. The process as claimed in claim 1, wherein the aromatic compound is 4,4'-diisopropylbiphenyl.

13. A process for the oxidation of an aromatic compound selected from benzene and biphenyl compounds containing at least one isopropyl group, which comprises the following consecutive steps:
(a) oxidizing the aromatic compound with molecular oxygen in the presence of an aqueous alkali solution in an oxidative reaction vessel, said vessel being made of nickel at parts thereof which come into contact with a reaction mixture;
(b) separating and recovering the aqueous alkali solution from the reaction mixture after the oxidative reaction (a), thereby collecting a solid matter;
(c) washing the soild matter with water so as to leach and eliminate carboxylic acids byproduced in the oxidative reaction (a);
(d) extracting the remaining solid matter with benzene or an alkyl benzene having at least one $C_{1-3}$ side chain; and
(e) cooling the resulting extract to isolate an aromatic compound selected from benzene and biphenyl compounds containing at least one 2-hydroxy-2-propyl group.

* * * * *